United States Patent
Wong

(10) Patent No.: US 7,514,574 B2
(45) Date of Patent: Apr. 7, 2009

(54) BIODEGRADABLE PENETRATION ENHANCERS WITH MULTIPLE HYDROPHILIC MOIETIES

(76) Inventor: Ooi Wong, 2236 Gomes Rd., Fremont, CA (US) 94539-4424

( * ) Notice: Subject to any disclaimer, the term of this patent is extended or adjusted under 35 U.S.C. 154(b) by 0 days.

(21) Appl. No.: 10/913,967

(22) Filed: Aug. 6, 2004

(65) Prior Publication Data
US 2005/0032893 A1 Feb. 10, 2005

Related U.S. Application Data

(60) Provisional application No. 60/493,619, filed on Aug. 7, 2003.

(51) Int. Cl.
*C07C 229/00* (2006.01)
(52) U.S. Cl. .................. 554/110; 554/103; 514/547
(58) Field of Classification Search .................. 554/103, 554/110
See application file for complete search history.

*Primary Examiner*—Deborah D Carr
(74) *Attorney, Agent, or Firm*—Bell & Associates; Richard Ekstrom

(57) ABSTRACT

Design of new, safe and effective biodegradable agents, which can cover a wide range of drug molecules in the transdermal permeation and other membranes absorption of physiologically active agents are disclosed. Biodegradable agents includes compounds having a multiple hydrophilic moiety groups which are water loving groups with general chemical structures provide for contributing the penetration enhancement characteristics such as glycolic group and N-alkyl substituted amino acidic group and a lipophilic moiety and also in contributing the balanced lipophilicity of the compounds such as long chain alkyl group are disclosed. More particularly, compounds with $R_1$, and $R_2$, as the steric hindered but can significantly affect the hydrolytic and enzymatic degradation or stability of the biodegradable enhancers. With these physical chemical features, the disclosed compound can influence the efficacy, toxicity, irritation, duration of action of the enhancers, and the reversibility of the skin, and the stability of the enhancers. The substituents also affect the final lipophilicity of the enhancers as the compounds will have higher partition coefficient values.

30 Claims, No Drawings

BIODEGRADABLE PENETRATION ENHANCERS WITH MULTIPLE HYDROPHILIC MOIETIES

This Formal Application claims a Priority Date of Aug. 7, 2003 benefited from a Provisional Patent Application 60/493, 619 file by the inventor of this patent application.

FIELD OF THE INVENTION

The invention relates to the design of safe and effective agents, which improve the rate of percutaneous and oral mucosal transport of physiologically active agents. More particularly, the present invention relates to improved topical penetration enhancer for use in the topical delivery of a local or systemic physiologically active agent to a mammalian organism.

BACKGROUND OF THE INVENTION

The scientific literature on transdermal drug delivery is a tremendous one (give references), which started many years ago. Cleary (1993) and Chien (1992) have reviewed this topic extensively. Because transdermal route of administering drugs has advantages over the traditional ways, there is much interest in the research and development in this field. However, most existing therapeutic agents do not readily penetrate the skin owing to the great penetration resistance of stratum corneum to absorption. Chien, 1992) (Walter, 1993) (Hadgraft, 1993) (Barry, 1983)(Hadgraft, 1989)

The transdermal route of drug administration offers a number of advantages over the more conventional routes of drug administration. For instance, a drug may be delivered to targeted tissues from adjacent skin areas. The transdermal route of drug administration also allows for a gradual, controlled release of drug into the systemic circulation. Since many drugs are poorly absorbed or delivered through the traditional routes of administration, the transdermal route provides an effective method of achieving improved bioavailability for those drugs. The transdermal route of drug administration is also advantageous since the administration of dermally administered drugs may be easily stopped should an undesirable side effect occur during therapy.

Dermal drug formulations may represent the oldest drug dosage form in human history. It is highly probable that even ancient people used resins and animal fats to treat damage to the skin resulting from injuries and burns. The use of such dermal formulations for local effect remained largely unchanged until the middle of this century. The concept of administering drugs through the skin to achieve a local or systemic effect was first seriously advocated by Dr. Alejandro Zaffaroni in the early 1970's. Since that time extensive research has been undertaken in this field. Thus, in the last two decades, a wide variety of compounds have been evaluated as to their effectiveness in enhancing the rate of penetration of drugs through the skin. The classically recognized strong enhancers tend to be proton accepting solvents, e.g., dimethyl sulfoxide (DMSO) and dimethyl acetamide (DMA). Recently, 2-pyrrolidone, N,N-diethyl-m-toluamide (Deet), 1-dodecylazacycloheptane-2-one (Azone, a registered trademark of Nelson Research), N,N-dimethylformamide, N-methyl-2-pyrrolidone and calcium thioglycolate have been reported as effective enhancers. A substantial outline comprising patent literature in the field of permeation enhancers is given by Santus and Baker (1993). Topical information dealing with the problem of skin absorption enhancers are reviewed by Kalbitz et al, (1996)

However, there is only a small number of pharmaceutical transdermal products has reached the market place with Scopolamine patch being the first. Until recently there is fewer than 10 products (Checked out) before 1985. And the main reasons are: there was only a limited number of suitable drug candidates that have the transport permeability suitable for transdermal preparation and very few penetration enhancers to assist these drug compounds. Most of the chemicals studied are either toxic or too irritating for use on human skin. Azone showed promising penetration enhancement for many drug molecules, however it is toxic and can cause skin irritation and it has not been approved for used in pharmaceutical preparation.

This invention is useful in transdermal drug delivery of physiological active drug molecules. It is also useful for enhancing the rectal, vaginal, ear, oral cavity and inhales absorption. It can be incorporated readily into the topical formulations such as creams, lotion, gel, ointments, suppository, spray, aerosol, buckle tablet or sublingual tablet or as a buckle, gingival, sublingual of transdermal patches and can provide fast drug action. In spite of the foregoing advantages, transdermal formulations are limited. They cannot be used with most polar drugs since they tend to penetrate the skin too slowly. This characteristic is particularly crucial since most drugs are of a polar character. In addition, many drugs elicit a reaction and/or irritation at the site of topical application.

Two methods are known for improving the rate of penetration of polar drugs across the skin. The first method is to make a better formulation of the drug to increase its thermodynamic activity. The thermodynamic activity of a drug in a dermal formulation is dependent on the concentration of the drug and the choice of the vehicle. According to the laws of thermodynamics, the maximum activity of the drug is usually fixed by that of the pure state, i.e., the drug crystal. The second method involves the use of compounds or penetration enhancers to increase the permeability of the barrier membrane. The latter method is generally more practical because of its convenience and effectiveness.

Higuchi and Pogany (1987) developed some non-biodegradable penetration new cyclic ureas, which were tested for transdermal penetration enhancement of indomethacin showing good enhancement. Ibuki (1987, Ph. D.thesis) investigated the series of cyclic ureas for the transdermal penetration enhancement of indomethacin in a petrolatum ointment dosage form. The results indicate that one of these cyclic ureas shows penetration enhancement two times of Azone. Unfortunately, this compound and Azone exhibited LD50 values of 136 and 232 mg/kg, respectively, when given i.p. to mice. Therefore these compounds might not be safe for practical uses.

Wong and Higuchi (refs) introduced a new class of biodegradable cyclic ureas as the penetration enhancers in 1987. The non-biodegradable version of cyclic ureas was found to be toxic (Ibuki). The idea of biodegradability was simple. Prior to degradation in the skin, the enhancers were able to penetrate the stratum corneum and enhance the drug molecules across the skin. And the enhancer was cleaved by enzyme, in this case, esterase. The enhancers were designed in such a way that they were degraded quickly and there is no accumulation of the enhancers in the skin thus causing toxicity or irritation. The synthesis of the cyclic ureas was difficult and needs many steps giving low yields of products. We then developed another class of enhancers, alkyl N,N-dialkylamino acetate. (Wong et al)

We know that the biodegradable concept works as expected. This has been demonstrated in the prior art (Wong et al, U.S. Pat. Nos. 4,845,233, 5,082,866, 49,803,788) (Hrabalek et al, U.S. Pat. No. 6,187,938) (Buyuktimkin et al, U.S. Pat. No. 6,118,020) (Friend et al U.S. Pat. No. 5,238,933) Biodegradable penetration enhancers all work well both in penetration enhancement and safety. There has been much research work done on alkyl N,N-dialkyl amino alkanoates. As the intact enhancers possessing the penetration characteristics (define and give examples) across the skin barrier they are fragmented and at the same time the drug molecule penetrates across the skin barrier. The smaller fragmented pieces are normally either lipophilic or hydrophilic moieties depending what the starting innocuous materials were used as the building blocks in the beginning. These fragments were removed quickly by the body and thus provide good safety profile.

Biodegradable penetration enhancers are definitely different from the other non-degradable enhancers. They disrupted the lipid bi-layer of the skin and this phenomenon reversed after several days of experiment as demonstrated by the DSC studies (Hirvonen et al, in the Press). Thermograms show that pretreatment of human stratum corneum with Azone and dodecanol also has 4 different typical endothermic peaks appear at 35, 70, 80, and 90° C. but these peaks never recovered or recovered too slowly or too small that beyond the detection limit of DSC. The first three peaks were partially reversible indicating a lipid origin, however, the endothermic peak at 90° C. indicates a protein origin. After application of enhancer on the skin the interaction is reversed after four days and the peaks at 35, 70, 80, and 90° C. reappeared. This is just as expected, the enhancers penetrated into deeper skin. The early recovery of the thermograms for the biodegradable enhancer indicates that its resident time in the skin was much shorter than those for the Azone and dodecanol. This is the reason for the reduction of toxicity and irritation of the enhancer. It is suggested that the shorter resident time of dodecyl N,N-dimethylamino acetate is related to the hydrophilicity of the hydrophilic moiety or the polar head group.

The difference between biodegradable and non-biodegradable

| | biodegradable | non-biodegradable |
|---|---|---|
| Enzyme cleavable | yes | no (Buyuktimkin et al, 1991) |
| Skin crossing | detected in the diff. cell | non detectable (Hirvonen et al) |
| Skin reversibility | yes | non or very slow (Hirvonen et al, 1993) |
| Toxicity reduction | yes | no (Wong et al, 1989) |
| Onset | usually fast | enhancer dependent (Wong et al, 1989) |

Many drugs of varying size require penetration enhancers for transport across the skin or mucous membranes. A number of problems and strategies for delivery of macromolecules have been documented in the literature but more effective penetration enhancers are needed in the formulation development. One approach to reducing toxicity involves biodegradable compounds which make use of the enzyme activity in the skin to fragment the penetration enhancers into smaller innocuous compounds. Amino acid esters of long chain alcohols were synthesized because they can be cleaved by the esterases into alcohol and substituted amino acids (Wong et al) (Buyuktimkin et al, 1991). (Wong et al, J. Pham. Sci., 1988) The transdermal route of administration is a superior way to deliver a drug in many circumstances ( ). However, most existing therapeutic agents do not readily penetrate the skin owing to the great resistance of the stratum corneum to absorption. A good approach to this problem is to use a penetration enhancer to reduce the skin resistance.

Bungaard et (1984) have studied the enzymatic hydrolysis of various amino acid esters in 80% human plasma and phosphate buffers with pH 7.4. The hydrolytic rates are structure dependent. This is very useful information as to which hydrophilic moiety to be used because it can affect the enhancement properties and safety of the compound. The data information applies to amino acid esters biodegradable enhancers The use of permeation enhancers or their combinations for transdermal administration of various drug(s) is described in numerous recent patents.

Improved Drug Permeation in Vitro and in Vivo by the Enhancers

There are a large number of substances interactions with the skin and its stratum corneum. Transdermal enhancers as substances used in pharmaceutical preparation have to meet a set of qualitative criteria. They must not be: toxic; irritate, allergic or sensitized to the skin; and they should be pharmacologically inert at the concentration required to exert adequate permeation action; their effect should be immediate, predictive and reversible; and they should be readily incorporated into pharmaceutical preparations. Many chemicals have been investigated for their ability to enhance the permeation of different drug molecules through the skin barrier (ref). Some are very effective. However, when the chemical structures are examined, there is no meaningful relationship can be drawn at this level. Molecular sizes as small as ethanol have been found to be effective as an enhancer and it has been used in Estraderm, an estuarial transdermal patch. It was the only transdermal product, which used an enhancer, ethanol in this case, compared to other products in the 1980's. Some of the enhancers, which had been investigated, are ethanol, DMSO, terpenes, DEET, Azone, Oleic acid, dodecanol. The enhancer research has gone through a dark period in which the active and physiological agents were not able to produce an effective product. (Hrabalek et al).

Recently, biodegradable penetration enhancers have been found useful in topical formulations in assisting a variety of drug candidates in permeating the skin barrier. The dialkyl amino alkanoates are now the major technology of Nexmed, a pharmaceutical company. Macrochem, another pharmaceutical company, also has its own biodegradable penetration enhancer system. Other biodegradable penetration enhancer system is the omega-amino acid derivative of Bochemie (CZ). There are other biodegradable enhancers being studied such as long chain alkyl esters, and alkyl esters of SRI International, and N-(2-hydroxyethyl)-2-pyrrolidones (Holland and Curry, 1993).

Lipophilic and Hydrophilic Moiety to Make Up Penetration Enhancers

When the enhancers in the literature are examined, there is no immediate straightforward relationship can be drawn. The molecular size can be as small as ethanol. And towards the other end, M W above 300 has been found to be effective. Generally these enhancers can be divided into two groups; (A) this group including smaller molecular weights without a typical molecular structure e.g. ethanol, DMSO, propylene glycol and DEET; and (B) these enhancers including compounds having a functional groups which are able to form hydrogen bond and are attached to a long alkyl chain which contributes the balanced lipophilicity with the functional group. Usually, the optimal lead compound of this mini series is one with alkyl chain approximately 12 carbons. This group can be further divided into two groups, (i) biodegradable and (ii) non-biodegradable penetration enhancers. The number of biodegradable enhancers is slowly increased recently. Another feature of the group (B) enhancers, it is easy to note that the enhancers have a polar head moiety and a lipophilic moiety. The hydrophilic moiety of the biodegradable enhancers can be replaced with some other moieties by some simple chemical synthesis modification.

What can this type of multiple hydrophilic moieties biodegradable penetration enhancers do? What advantages do they have over the present ones? What is the purpose of the present invention?

All the hydrophilic moieties can form hydrogen bonding and they usually consist of hydroxyl, —OH; amino, —$NH_2$; sulphuryl, —SH; keto, —CO; amide, —CONH— and many others. It is known that hydrogen bond formation is a very important factor affecting the solubilization of the solute. Therefore, the two hydrophilic moieties chosen in this invention both can form hydrogen bondings with drug molecules, they are propylene glycol and alkyl substituted amino acid. The advantage of the present invention is to extend the hydrophilicity so that an optimized compound can be easily identified and can reach out for more drug candidates for transferal delivery. Also, the enzyme catalyzed hydrolysis kinetics will be altered to a more suitable range. The hydrophilicity of a biodegradable enhancer is limited by the polar head group or the hydrophilic moiety and can be changed by adding a second hydrophilic moiety onto the enhancer system. Intuitively, one could introduce more hydrophilicity into the enhancer system is the basis of the present invention to design a two hydrophilic moieties biodegradable penetration enhancer systems, see the Figure given earlier.

Hirvonen et al (1993) have reported the enhanced skin permeability of tritiated water and other drug compounds by several enhancers. Comparing the enhanced $T_2O$ flux through human cadaver skin over the passive flux, it was reported that Azone increases the skin permeability to $T_2O$ by 8 times and dodedyl, (N,N-dimethyl amino) acetate by 13 times. It was suggested that the mechanism of the biodegradable enhancer is probably due to increased partitioning and diffusion rates of the drug. As it has been discussed early on, the polar head group of the enhancer play very important role in the penetration enhancement effects and safety. The difference between Azone and dodecyl (N N-dimethyl amino) acetate (DDAA) is in their polar heads, while both have 12 carbon alkyl chain. Azone has a cyclic 7 membered amide ring while DDAA has an amino acid hydrophilic polar head group. Both can form different hydrogen bodings of different nature with different bond strength of energy. The amino acidic polar head group can form stronger hydrogen bond than the cyclic amide, (March, 1985) larger amount of water get into the skin media and thus higher water penetration rate of $T_2O$. This could be part of the major cause of reduction of skin resistance to drug penetration.

Literature Information

- Hydrolytic kinetic must be sorted out early on and this information is very important. This physical chemical property an important one. It determines the resident time of the biodegradable penetration enhancer in the skin and the hydrolytic kinetics of the enhancer must adequate to produce the right time. This also can be used in programming the delivery profile of a transdermal delivery system.
- The biodegradable penetration enhancer has not yet been optimized. This would require studying the penetration enhancement versus a series of the compounds with different lipophilicity by changing the alkyl chain length. It is also needed to investigate the hydrophilicity of the same series versus the penetration enhancement. This will require a biodegradable penetration enhancers system that can extend.
- How much lipohilicity and hydrophilicity is required to give the best biodegradable enhancer.
- The enhancer is to penetrate fast enough the stratum cornea, loosen up the well orientated lipid layer, the hydrophilic moiety.
- This can bring in the water molecules, so in the absence of biodegradable enhancer. When this happens the penetration resistance of the skin reduces and the drug molecules diffuse faster
- The hydrophilicity of the enhancer can increase the solubility of the drug molecules.
- The bioreversibility of the enhancers can reverse the skin reaction in four days later. This can be confirmed by the Differential Scanning Calorimetry. This is a very important feature found only in the biodegradable series of penetration enhancers.

DESCRIPTION OF THE INVENTION

Many new biodegradable penetration enhancers can be designed by changing the building blocks of the bioreversible groups or the hydrophilic groups shown in the following diagram. All these enhancers will have different characteristics and function differently as needed when used in the pharmaceutical product formulation development. Given the probable balanced lipophilicity of the compounds one will expect the compound to have penetration enhancement for drug molecules, as this has been shown by other known biodegradable penetration enhancers in the prior art (Wong et al, 1990, 1992) (Fleeker et al, 1988), (Higuchi and Wong, 1989) (Bujuktimkin et al, 2000) (Hrabalek et al. 2001) (Holland and Curry, 1993). When the enhancers are probably designed they should have some of or all the properties to carry out a number of functions: penetration enhancement, solubility enhancement, partitioning enhancement, the ability of disrupting the lipid bi-layer of the stratum corneum of the skin, the ability to reverse the skin interaction with the enhancer, and to increase water content in the skin medium so that the drug molecules can diffuse at a higher rate while crossing the skin. N-Alkyl substituted amino acid ester groups have been used as an effective bioreversible group in the prior art (Wong et al)(Buyuktimkin et al) to make outstanding biodegradable enhancers.

The enhancer works out accordingly as expected. This hydrophilic moiety (N,N-dimethyl amino acetate), has been used in prodrugs design (Hans Bungaard 1984). The balanced hydrophilicity in alkyl N,N-dialkylamino acetates series of biodegradable enhancers has only been investigated briefly, there was no linear relationship being observed for the balanced lipophilicity and the penetration enhancement (Buyuktimkin et al, 1991) However, the relationship could be a parabolic type as this has been shown by Tsuzuki et al (1988) in a series of aliphatic alcohols. The penetration enhancement of indomethacin is a parabolic relationship with the number of carbon atom number of a series of straight chain alcohols. The parabolic relationship between the biological activities or responses and the lipophilicity of compounds of the same series is very common in biological systems (Hansch et al, 1965). In fact when the data of Buyuktimkin et al (1991) on the pKa and Rm values of their short series of alkyl N,N-dimethylamino acetates were plotted, it appears that a parabolic relationship on the left hand side of a whole parabolic relationship can be seen. Because the optimal compound in this series has not been found, therefore the amino acetate biodegradable penetration enhancers have not been optimized. The amino acid ester group can replace the bioreversible carrier B shown in the following figure. It is intuitive that by adding more hydrophilic group into the enhancer, it will also change the properties of the molecule further and therefore will cover more ground. In this way it is easier to reach the optimum compound of the series. In selecting the second hydrophilic group a very good choice is selection of a glycolic group. Propylene glycol is non-toxic and non-irritating, and it is a very good solvent for many drug compounds so that the enhancers can cover more widely including the newly developed drug candidates.

The biodegradable penetration enhancers were depicted in the following diagram:

Lipophilic moiety --- bioreversible carrier A ---- bioreversible carrier B
     ↓           ↓  esterase   ↓  esterase
Aliphatic acid    Carrier A    Carrier B After exerting their function, the enhancers were hydrolyzed by the skin enzyme into the nontoxic starting materials. Esterases are available in most part of the body (ref) and therefore in the present design of these penetration enhancers we combined the building blocks with ester functional groups.

The invention relates to the design of new, safe and effective biodegradable agents, which can cover a wide range of drug molecules in the transdermal permeation and other membranes absorption of physiologically active agents. More particularly, this invention relates to the compounds having a multiple hydrophilic moiety groups which are water loving groups as shown in the following general chemical structures and which are very important in contributing penetration enhancement characteristics such as glycolic group and N-alkyl substituted amino acidic group and a lipophilic moiety in contributing the balanced lipophilicity of the compounds such as long chain alkyl group which may or may not have an unsaturated functional group as given in the general structure (I). The balanced lipophilicity of the compounds determines the functions and safety of the compounds.

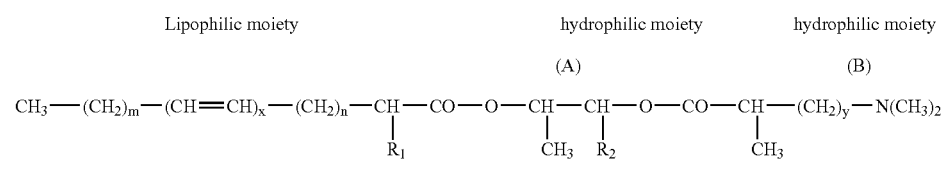

(I)

Lipophilic moiety      hydrophilic moiety    hydrophilic moiety
                               (A)                (B)

$CH_3-(CH_2)_m-(CH=CH)_x-(CH_2)_n-CH(R_1)-CO-O-CH(CH_3)-CH(R_2)-O-CO-CH(CH_3)-(CH_2)_y-N(CH_3)_2$

The General Chemical Structures of Biodegradable Penetration Enhancers

In general structure (I), $R_1$ and $R_2$ are selected from hydrogen or an alkyl group; m is a whole number from 0 to 12; n is a whole number from 0 to 12; x is a whole number from 0 to 3; and y is a whole number from 0 to 5. The compounds of the invention may be formulated in a pharmaceutical composition for topical administration of a pharmacologically active topical medicament, the composition being formulated, for example, as a cream, lotion, gel, ointment, suppository, spray, aerosol, buckle tablet or sublingual tablet, or as a buckle, gingival, sublingual or transdermal patch. The composition comprises: (a) a pharmacologically active topical medicament in an amount sufficient to achieve a desired pharmacological effect; and (b) a skin penetration enhancing compound of the general structure (I).

For example,

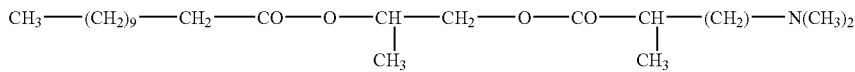

$CH_3-(CH_2)_9-CH_2-CO-O-CH(CH_3)-CH_2-O-CO-CH(CH_3)-(CH_2)-N(CH_3)_2$

N,N-Dimethylamino Isopropyl, Propylene Glycol Laurate (e.g. (I); $R_1=R_2=H$; m=9; n=1; x=0; y=1)

The $R_1$, and $R_2$, are the steric hindered but very important groups that can affect the hydrolytic and enzymatic degradation or stability of the biodegradable enhancers. This is very important physical chemical feature, which will influence the efficacy, toxicity, irritation, duration of action of the enhancers, and the reversibility of the skin, and the stability of the enhancers. The substituents also affect the final lipophilicity of the enhancers as the compounds will have higher partition coefficient values.

Additional examples of compounds of the invention are listed below. Any of these compounds may be formulation in a composition comprising the particular compound and a pharmacologically active topical medicament.

(a) The compound of general structure (I) wherein $R_1$ is hydrogen; $R_2$ is hydrogen; m=10; n=4; x=0; and y=1. This compound may be referred to as (N,N-dimethyl amino) isopropyl propylene glycol heptadecanoate.

(b) The compound of general structure (I) wherein $R_1$ is hydrogen; $R_2$ is hydrogen; m=8; n=4; x=0; and y=1. This compound may be referred to as (N,N-dimethylamino) isopropyl propylene glycol pentadecanoate.

(c) The compound of general structure (I) wherein $R_1$ is hydrogen; $R_2$ is hydrogen; m=6; n=4; x=0; and y=1. This compound may be referred to as (N,N-dimethylamino) isopropyl propylene glycol tridecanoate.

(d) The compound of general structure (I) wherein $R_1$ is hydrogen; $R_2$ is hydrogen; m=4; n=4; x=0; and y=1. This compound may be referred to as (N,N-dimethylamino) isopropyl propylene glycol undecanoate.

(e) The compound of general structure (I) wherein $R_1$ is hydrogen; $R_2$ is hydrogen; m=2; n=4; x=0; and y=1. This compound may be referred to as (N,N-dimethylamino) isopropyl propylene glycol nonanoate.

(f) The compound of general structure (I) wherein $R_1$ is hydrogen; $R_2$ is hydrogen; m=10; n=4; x=0; and y=2. This compound may be referred to as (N,N-dimethylamino) 2-isobutyl propylene glycol heptadecanoate.

(g) The compound of general structure (I) wherein $R_1$ is hydrogen; $R_2$ is hydrogen; m=8; n=4; x=0; and y=2. This compound may be referred to as (N,N-dimethylamino) 2-isobutyl propylene glycol pentadecanoate.

(h) The compound of general structure (I) wherein $R_1$ is hydrogen; $R_2$ is hydrogen; m=6; n=4; x=0; and y=2. This compound may be referred to as (N,N-dimethylamino) 2-isobutyl propylene glycol tridecanoate.

(i) The compound of general structure (I) wherein $R_1$ is hydrogen; $R_2$ is hydrogen; m=4; n=4; x=0; and y=2. This compound may be referred to as (N,N-dimethylamino) 2-isobutyl propylene glycol undecanoate.

(j) The compound of general structure (I) wherein $R_1$ is hydrogen; $R_2$ is hydrogen; m=3; n=3; x=0; and y=2. This compound may be referred to as (N,N-dimethylamino) 2-isobutyl propylene glycol nonanoate.

(k) The compound of general structure (I) wherein $R_1$ is methyl; $R_2$ is hydrogen; m=10; n=4; x=0; and y=1. This compound may be referred to as (N,N-dimethylamino) isopropyl propylene glycol 2-methyl-heptadecanoate.

(l) The compound of general structure (I) wherein $R_1$ is methyl; $R_2$ is hydrogen; m=8; n=4; x=0; and y=1. This compound may be referred to as (N,N-dimethylamino) isopropyl propylene glycol 2-methyl-pentadecanoate.

(m) The compound of general structure (I) wherein $R_1$ is methyl; $R_2$ is hydrogen; m=6; n=4; x=0; and y=1. This compound may be referred to as (N,N-dimethylamino) isopropyl propylene glycol 2-methyl-tridecanoate.

(n) The compound of general structure (I) wherein $R_1$ is methyl; $R_2$ is hydrogen; m=4; n=4; x=0; and y=1. This compound may be referred to as (N,N-dimethylamino) isopropyl propylene glycol 2-methyl-undecanoate.

(o) The compound of general structure (I) wherein $R_1$ is methyl; $R_2$ is hydrogen; m=3; n=3; x=0; and y=1. This compound may be referred to as (N,N-dimethylamino) isopropyl propylene glycol 2-methyl-nonanoate.

(p) The compound of general structure (I) wherein $R_1$ is methyl; $R_2$ is methyl; m=8; n=6; x=0; and y=2. This compound may be referred to as (N,N-dimethylamino) 2-isobutyl dimethyl-ethylene glycol 2-methyl-heptadecanoate.

(q) The compound of general structure (I) wherein $R_1$ is methyl; $R_2$ is methyl; m=7; n=5; x=0; and y=2. This compound may be referred to as (N,N-dimethylamino) 2-isobutyl dimethyl-ethylene glycol 2-methyl-pentadecanoate.

(r) The compound of general structure (I) wherein $R_1$ is methyl; $R_2$ is methyl; m=6; n=4; x=0; and y=2. This compound may be referred to as (N,N-dimethylamino) 2-isobutyl dimethyl-ethylene glycol 2-methyl-tridecanoate.

(s) The compound of general structure (I) wherein $R_1$ is methyl; $R_2$ is methyl; m=5; n=4; x=0; and y=2. This compound may be referred to as (N,N-dimethylamino) 2-isobutyl dimethyl-ethylene glycol 2-methyl-dodecanoate.

(t) The compound of general structure (I) wherein $R_1$ is hydrogen; $R_2$ is hydrogen; m=8; n=8; x=1; and y=1. This compound may be referred to as (N,N-dimethylamino) isopropyl propylene glycol 1 1-henicosenoate.

(u) The compound of general structure (I) wherein $R_1$ is hydrogen; $R_2$ is hydrogen; m=7; n=7; x=1; and y=1. This compound may be referred to as (N,N-dimethylamino) isopropyl propylene glycol 10-nonadecenoate.

(v) The compound of general structure (I) wherein $R_1$ is hydrogen; $R_2$ is hydrogen; m=6; n=6; x=1; and y=1. This compound may be referred to as (N,N-dimethylamino) isopropyl propylene glycol 9-heptadecenoate.

(w) The compound of general structure (I) wherein $R_1$ is hydrogen; $R_2$ is hydrogen; m=5; n=5; x=1; and y=1. This compound may be referred to as (N,N-dimethylamino) isopropyl propylene glycol 8-pentadecenoate.

(x) The compound of general structure (I) wherein $R_1$ is methyl; $R_2$ is methyl; m=8; n=8; x=1; and y=1. This compound may be referred to as (N,N-dimethylamino) isopropyl dimethyl-ethylene glycol 2-methyl-11-heneicosenoate.

(y) The compound of general structure (I) wherein $R_1$ is methyl; $R_2$ is methyl; m=7; n=7; x=1; and y=1. This compound may be referred to as (N,N-dimethylamino) isopropyl dimethyl-ethylene glycol 2-methyl-10-nonadecenoate.

(z) The compound of general structure (I) wherein $R_1$ is methyl; $R_2$ is methyl; m=6; n=6; x=1; and y=1. This compound may be referred to as (N,N-dimethylamino) isopropyl dimethyl-ethylene glycol 2-methyl-9-heptadecenoate.

(aa) The compound of general structure (I) wherein $R_1$ is methyl; $R_2$ is methyl; m=5; n=5; x=1; and y=1. This compound may be referred to as (N,N-dimethylamino) isopropyl dimethyl-ethylene glycol 2-methyl-8-pantadecenoate.

(bb) The compound of general structure (I) wherein $R_1$ is methyl; $R_2$ is methyl; m=4; n=4; x=1; and y=1. This compound may be referred to as (N,N-dimethylamino) isopropyl dimethyl-ethylene glycol 2-methyl-7-tridecenoate.

This invention relates to the preparation of the compounds according to the following simplified synthetic reactions. The (N,N-dimethyl) amino isopropyl formyl chloride reacts with the propylene to give propylene glycol ester intermediate. Reaction of the long chain alkyl acyl chloride with the intermediate gives the desired product.

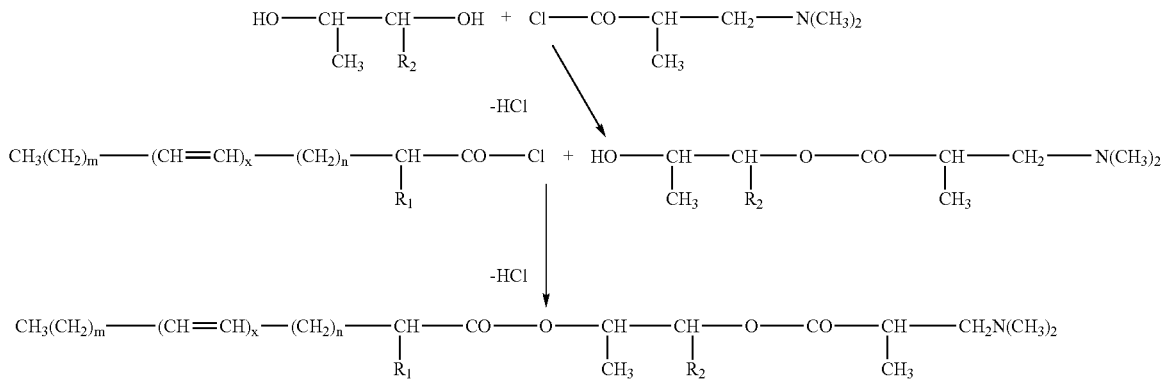

This invention relates to the method of uses in transdermal delivery through the skin and other membranes of older persons.

Although the present invention has been described in terms of the presently preferred examples and embodiments, it is to be understood that such disclosure is not to be interpreted as limiting. Various alterations and modifications will no doubt become apparent to those skilled in the art after reading the above disclosure. Accordingly, it is intended that the appended claims be interpreted as covering all alterations and modifications as fall within the true spirit and scope of the invention.

What is claimed is:

1. A compound having a general chemical structure represented by a formula (I):

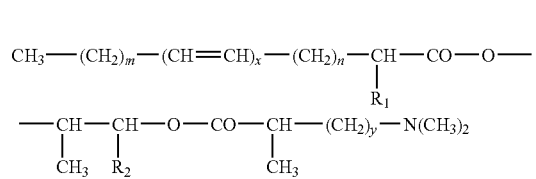

wherein $R_1$ and $R_2$ are either hydrogen or an alkyl group; m is a whole number from 0 to 12;
n is a whole number from 0 to 12; x is a whole number from 0 to 3; and y is a whole number from 0 to 5.

2. A composition comprising:
(a) a pharmacologically active topical medicament; and
(b) a compound of formula (I) of claim 1 wherein $R_1$ is hydrogen; $R_2$ is hydrogen; m=9; n=1; x=0; and y=1.

3. A composition comprising:
(a) a pharmacologically active topical medicament; and
(b) a compound of formula (I) of claim 1 wherein $R_1$ is hydrogen; $R_2$ is hydrogen; m=10; n=4; x=0; and y=1.

4. A composition comprising:
(a) a pharmacologically active topical medicament; and
(b) a compound of formula (I) of claim 1 wherein $R_1$ is hydrogen; $R_2$ is hydrogen; M=8; n=4; x=0; and y=1.

5. A composition comprising:
(a) a pharmacologically active topical medicament; and
(b) a compound of formula (I) of claim 1 wherein $R_1$ is hydrogen; $R_2$ is hydrogen; m=6; n=4; x=0; and y=1.

6. A composition comprising:
(a) a pharmacologically active topical medicament; and
(b) a compound of formula (I) of claim 1 wherein $R_1$ is hydrogen; $R_2$ is hydrogen; m=4; n=4; x=0; and y=1.

7. A composition comprising:
(a) a pharmacologically active topical medicament; and
(b) a compound of formula (I) of claim 1 wherein $R_1$ is hydrogen; $R_2$ is hydrogen; M=2; n=4; x=0; and y=1.

8. A composition comprising:
(a) a pharmacologically active topical medicament; and
(b) a compound of formula (I) of claim 1 wherein $R_1$ is hydrogen; $R_2$ is hydrogen; M=10; n=4; x=0; and y=2.

9. A composition comprising:
(a) a pharmacologically active topical medicament; and
(b) a compound of formula (I) of claim 1 wherein $R_1$ is hydrogen; $R_2$ is hydrogen; m=8; n=4; x=0; and y=2.

10. A composition comprising:
(a) a pharmacologically active topical medicament; and
(b) a compound of formula (I) of claim 1 wherein $R_1$ is hydrogen; $R_2$ is hydrogen; M=6; n=4; x=0; and y=2.

11. A composition comprising:
(a) a pharmacologically active topical medicament; and
(b) a compound of formula (I) of claim 1 wherein $R_1$ is hydrogen; $R_2$ is hydrogen; m=4; n=4; x=0; and y=2.

12. A composition comprising:
(a) a pharmacologically active topical medicament; and
(b) a compound of formula (I) of claim 1 wherein $R_1$ is hydrogen; $R_2$ is hydrogen; m=3; m=3; x=0; and y=2.

13. A composition comprising:
(a) a pharmacologically active topical medicament; and
(b) a compound of formula (I) of claim 1 wherein $R_1$ is methyl; $R_2$ is hydrogen; M=10; n=4; x=0; and y=1.

14. A composition comprising:
(a) a pharmacologically active topical medicament; and
(b) a compound of formula (I) of claim 1 wherein $R_1$ is methyl; $R_2$ is hydrogen; m=8; n=4; x=0; and y=1.

15. A composition comprising:
(a) a pharmacologically active topical medicament; and
(b) a compound of formula (I ) of claim 1 wherein $R_1$ is methyl; $R_2$ is hydrogen; m=6; n=4; x=0; and y=1.

16. A composition comprising:
(a) a pharmacologically active topical medicament; and
(b) a compound of formula (I) of claim 1 wherein $R_1$ is methyl; $R_2$ is hydrogen; m=4; n=4; x=0; and y=1.

17. A composition comprising:
(a) a pharmacologically active topical medicament; and
(b) a compound of formula (I) of claim 1 wherein $R_1$ is methyl; $R_2$ is hydrogen; m=3; n=3; x=0; and y=1.

18. A composition comprising:
(a) a pharmacologically active topical medicament; and
(b) a compound of formula (I) of claim 1 wherein $R_1$ is methyl; $R_2$ is methyl; m=8; n=6; x=0; and y=2.

19. A composition comprising:
(a) a pharmacologically active topical medicament; and
(b) a compound of formula (I) of claim 1 wherein $R_1$ is methyl; $R_2$ is methyl; m=7; N=5; x=0; and y=2.

20. A composition comprising:
(a) a pharmacologically active topical medicament; and
(b) a compound of formula (I) of claim 1 wherein $R_1$ is methyl; $R_2$ is methyl; m=6; n=4; x=0; and y=2.

21. A composition comprising:
(a) a pharmacologically active topical medicament; and
(b) a compound of formula (I) of claim 1 wherein $R_1$ is methyl; $R_2$ is methyl; m=5; n=4; x=0; and y=2.

22. A composition comprising:
(a) a pharmacologically active topical medicament; and
(b) a compound of formula (I) of claim 1 wherein $R_1$ is hydrogen; $R_2$ is hydrogen; M=8; n=8;x=1; and y=1.

23. A composition comprising:
(a) a pharmacologically active topical medicament; and
(b) a compound of formula (I) of claim 1 wherein $R_1$ is hydrogen; $R_2$ is hydrogen; M=7; n=7;x=1; and y=1.

24. A composition comprising:
(a) a pharmacologically active topical medicament; and
(b) a compound of formula (I) of claim 1 wherein $R_1$ is hydrogen; $R_2$ is hydrogen; m=6; n=6;x=1; and y=1.

25. A composition comprising:
(a) a pharmacologically active topical medicament; and
(b) a compound of formula (I) of claim 1 wherein $R_1$ is hydrogen; $R_2$ is hydrogen; M=5; n=5;x=1; and y=1.

26. A composition comprising:
(a) a pharmacologically active topical medicament; and
(b) a compound of formula (I) of claim 1 wherein $R_1$ is methyl; $R_2$ is methyl; m=8; n=8; x=1; and y=1.

27. A composition comprising:
(a) a pharmacologically active topical medicament; and
(b) a compound of formula (I) of claim 1 wherein $R_1$ is methyl; $R_2$ is methyl; m=7; n=7; x=1; and y=1.

28. A composition comprising:
(a) a pharmacologically active topical medicament; and
(b) a compound of formula (I) of claim 1 wherein $R_1$ is methyl; $R_2$ is methyl; m=6; N=6; x=1; and y=1.

29. A composition comprising:
(a) a pharmacologically active topical medicament; and
(b) a compound of formula (I) of claim 1 wherein $R_1$ is methyl; $R_2$ is methyl; m=5; N=5; x=1; and y=1.

30. A composition comprising:
(a) a pharmacologically active topical medicament; and
(b) a compound of formula (I) of claim 1 wherein $R_1$ is methyl; $R_2$ is methyl; m=4; n=4; x=1; and y=1.

\* \* \* \* \*